US011756401B2

(12) United States Patent
Pasupuleti et al.

(10) Patent No.: US 11,756,401 B2
(45) Date of Patent: Sep. 12, 2023

(54) NEURAL NETWORK BASED RADIOWAVE MONITORING OF FALL CHARACTERISTICS IN INJURY DIAGNOSIS

(71) Applicant: VENTECH SOLUTIONS, INC., Columbus, OH (US)

(72) Inventors: Ravi Kiran Pasupuleti, Triplicane Chennai (IN); Ravi Kunduru, Columbus, OH (US)

(73) Assignee: Ventech Solutions, Inc., Columbus, OH (US)

( * ) Notice: Subject to any disclaimer, the term of this patent is extended or adjusted under 35 U.S.C. 154(b) by 0 days.

(21) Appl. No.: 17/974,936

(22) Filed: Oct. 27, 2022

(65) Prior Publication Data

US 2023/0048309 A1 Feb. 16, 2023

Related U.S. Application Data

(63) Continuation of application No. 16/829,794, filed on Mar. 25, 2020, now Pat. No. 11,568,262.

(51) Int. Cl.

| | |
|---|---|
| *G06N 20/00* | (2019.01) |
| *G06V 30/194* | (2022.01) |
| *G06N 3/084* | (2023.01) |
| *G06V 10/764* | (2022.01) |
| *G06V 10/82* | (2022.01) |
| *G08B 21/04* | (2006.01) |
| *A61B 5/00* | (2006.01) |
| (Continued) | |

(52) U.S. Cl.
CPC .......... *G08B 21/043* (2013.01); *A61B 5/1117* (2013.01); *A61B 5/7246* (2013.01); *A61B 5/7267* (2013.01); *G06N 3/084* (2013.01);

| | |
|---|---|
| *G06N 20/00* | (2019.01); *G06V 10/764* |
| (2022.01); *G06V 10/82* (2022.01); *G06V* | |
| *30/194* (2022.01); *G06V 30/1916* (2022.01); | |
| *G06V 40/23* (2022.01); *A61B 2562/0223* | |
| | (2013.01) |

(58) Field of Classification Search
None
See application file for complete search history.

(56) References Cited

U.S. PATENT DOCUMENTS

| 10,009,666 B1 | 6/2018 | van Scheltinga |
|---|---|---|
| 10,319,209 B2 | 6/2019 | Carlton-Foss |
| (Continued) | | |

*Primary Examiner* — Idowu O Osifade
(74) *Attorney, Agent, or Firm* — MAHAMEDI IP LAW LLP (57) ABSTRACT

System and method of deploying a trained machine learning neural network (MLNN) in generating a fall injury condition of a subject. The method comprises receiving, at input layers of the trained MLNN, millimeter wave (mmWave) radar point cloud data representing fall attributes from monitoring the subject via mmWave radar sensing device, the input layers associated with the fall attributes, receiving, at a second set of input layers, personal attributes of the subject associated with ones of the second set of input layers, the first and second sets of input layers interconnected with an output layer of the trained MLNN via intermediate layers, the trained MLNN produced by establishing a correlation between an injury condition of prior subjects and mmWave point cloud data and personal attributes associated with the prior subjects, and generating, at the output layer, the fall injury condition attributable to the subject.

20 Claims, 4 Drawing Sheets

(51) Int. Cl.
   *A61B 5/11*     (2006.01)
   *G06V 30/19*    (2022.01)
   *G06V 40/20*    (2022.01)

(56) References Cited

U.S. PATENT DOCUMENTS

| | | |
|---|---|---|
| 11,043,219 B1 | 6/2021 | Walters |
| 2008/0079989 A1 | 4/2008 | Agnetta |
| 2009/0076419 A1 | 3/2009 | Namieni |
| 2009/0210419 A1 | 8/2009 | Chitnis et al. |
| 2010/0201378 A1 | 8/2010 | Costanzo |
| 2011/0018657 A1 | 1/2011 | Cheng |
| 2012/0319821 A1 | 12/2012 | Karttaavi |
| 2014/0121527 A1 | 5/2014 | Adler, Jr. |
| 2014/0221825 A1 | 8/2014 | Mahfouz |
| 2015/0248536 A1 | 9/2015 | Tawil |
| 2017/0224253 A1 | 8/2017 | Berlin et al. |
| 2017/0238867 A1 | 8/2017 | Javed et al. |
| 2018/0144465 A1 | 5/2018 | Hsieh |
| 2018/0177436 A1 | 6/2018 | Chang |
| 2018/0199996 A1 | 7/2018 | Hogan |
| 2019/0104982 A1 | 4/2019 | Dunn |
| 2019/0180174 A1 | 6/2019 | Koswatta |
| 2020/0113488 A1 | 4/2020 | Al-Ali |
| 2020/0250387 A1 | 8/2020 | Hiraoka |
| 2021/0043205 A1 | 2/2021 | Lee |
| 2021/0192762 A1* | 6/2021 | Guan ............... G06V 20/647 |
| 2021/0225378 A1 | 7/2021 | Montemurro |
| 2022/0139070 A1* | 5/2022 | Okamoto ........... G06V 20/54  382/159 |

* cited by examiner

Receiving, in a first set of input layers of the MLNN, from a millimeter wave (mmWave) radar sensing device, a set of mmWave radar point cloud data representing respective ones of a set of fall attributes associated with a subject, each of the first set of input layers being associated with the respective ones of the set of fall attributes
310

↓

Receiving, at a second set of input layers of the MLNN, a set of personal attributes of the subject, each of the set of personal attributes being associated with a respective one of the second set of input layers, the first and second sets of input layers being interconnected with an output layer of the MLNN via at least one intermediate layer, the at least one intermediate layer configured in accordance with an initial matrix of weights, the first and second sets of input layers, the at least one intermediate and output layers of the MLNN being implemented, using the one or more processors, in a memory of the computing device
320

↓

Training a MLNN classifier in accordance with a supervised training that establishes a correlation between at least one injury condition of the subject as generated at the output layer and the sets of mmWave point cloud data and personal attributes
330

↓

Adjusting the initial matrix of weights by backpropagation thereby to increase the correlation between the at least one injury condition and the sets of mmWave point cloud data and personal attributes
340

NEURAL NETWORK BASED RADIOWAVE MONITORING OF FALL CHARACTERISTICS IN INJURY DIAGNOSIS

CROSS-REFERENCE TO RELATED APPLICATIONS

This application is a continuation of U.S. patent application Ser. No. 16/829,794 filed on Mar. 25, 2020; the aforementioned priority application being hereby incorporated by reference in its entirety herein.

TECHNICAL FIELD

The disclosure herein relates to deep learning network systems for radiowave monitoring of fall characteristics in diagnosing patient injuries.

BACKGROUND OF THE INVENTION

Falls are a major problem among elderly as well as medical patients and other individuals experiencing subpar health. Despite many efforts in elderly care institutions and in hospitals, falls pose a serious health risk. Complicating the detection and treatment of falls, current trends are that most senior citizens prefer to live at home, where, oftentimes they are alone, making timely fall detection, fall injury diagnosis and treatment more difficult, leading to increased risk of injury and debilitation. Fall injuries can include broken bones, sprained ankles or wrists, knee damage, shoulder dislocations or muscle strains, cuts and bruises, spine and nerve damage from being overstretched from a fall. Traumatic brain injury can result from a fall even when the subject's head does not hit the ground, but rather from the brain receiving a jolt without direct impact. Monitoring an elderly person 24 hours a day presents a challenge to caregivers, whose attention must be shared typically among multiple residents. As people age, they become more likely to fall, even as their body becomes more vulnerable, with a consequence that they become more likely to sustain significant injury when they fall.

DETAILED DESCRIPTION

Methods and systems provided herein, among other advantages and benefits, to apply millimeter wave (mmWave) radar radio-frequency (RF) based sensing technologies to monitor fall patterns and fall characteristics of human subjects in falls. In particular, via supervised training of a machine learning neural network (MLNN), correlating fall characteristics of human subjects, based on mmWave radar sensing, with observed or actual fall injuries resulting. Preparatory to diagnosing or predicting fall injury conditions, the MLNN system is subjected to a supervised training regimen. During the training, fall characteristics including dynamic fall parameters or attributes in conjunction with personal attributes of subjects are correlated with observed fall injuries. The dynamic fall attributes are represented in accordance with mmWave radar point cloud data as sensed during a fall and upon impact with a surface. Measurable or observable features and characteristics corresponding to the fall attributes can include identification of an anatomical member that receives an impact upon falling, a speed at which the anatomical member receives the impact, an orientation of the anatomical member upon receiving the impact, an angular speed of rotation at which the anatomical member receives the impact, in embodiments. In embodiments, motion vectors and posture vectors are computed based on sensed mmWave point cloud data that provides an observed time series of bodily portions or members during a fall.

Advantageously, upon deployment, the trained machine learning neural network is capable of ascertaining and predicting fall injury conditions based on mmWave radar-sensed fall attributes in conjunction with personal attributes of the fall subject or medical patient.

Millimeter wave radar sensing technology as described and applied herein refers to detection of objects and providing information on range, velocity and angle of those objects. mmWave radar uses a contactless technology which operates in the spectrum between 30 GHz and 300 GHz, having inherent small wavelengths that provide sub-mm range accuracy while able to penetrate materials such as plastic, drywall, clothing, and being impervious to environmental conditions like rain, fog, dust and snow. As opposed to commercial radar techniques, the disclosure herein implements a high-resolution mmWave radar sensor to obtain a relatively richer radar point cloud representation for tracking and monitoring of a medical patient anatomical features, limbs and extremities. Advantageously, in embodiments implemented herein, 60-GHz mmWave sensors provide 4 GHz of UWB bandwidth, resulting in 16 times the available bandwidth than 24-GHz sensors for high-accuracy mmWave radar applications.

As referred to herein, a point cloud refers to a set of data points in space. As the output of 3D scanning processes, in this case a mmWave 3D scanning and sensing operations, point clouds are used to capture anatomical feature data of the human subject. mm Wave radar, based on the principle of frequency modulated continuous wave (FMCW) radar, has the ability to simultaneously measure range and relative radial speed of a target point. A mmWave radar sensor is applied herein to produce point clouds, of varying density of data points in embodiments, by making repeated measurements as the body and body members of a medical patient or subject moves, each time acquiring the motion data, correlated via timestamping as progressively sensed, from a different viewpoint or perspective. mm Wave sensor devices transmit an RF signal and record reflection from the target point that is collected in the point cloud, the point cloud data including an object range, angle, velocity, signal strength delivered, and optionally a pre-designated subject ID in one embodiment, over a computing and communication interface. The subject ID may be a patient ID in some embodiments. In embodiments herein, the point cloud data can encapsulate fall dynamics in conjunction with progressive timestamps correlated with the fall data, such that fall dynamic parameters or attributes can be determined, such as but not limited to identification of an anatomical member that receives an impact upon falling, a speed at which the anatomical member receives the impact, an orientation of the anatomical member upon receiving the impact, an angular speed of rotation at which the anatomical member receives the impact, and even a compliance attribute of a surface at which the impact is received. In this manner, the point cloud data as sensed provides an observed time series of bodily portions or members during a fall.

Dynamic parameters associated with a falling subject, also referred to herein as fall attributes, as sensed via mmWave radar and encoded via the point cloud data can include identification of an anatomical member that receives an impact upon falling, a speed at which the anatomical member receives the impact, an orientation of the anatomical member upon receiving the impact, an angular speed of rotation at which the anatomical member receives the impact, and even a compliance attribute of a surface at which the impact is received.

As described herein, the neural networks, in embodiments, refer to an artificial intelligence (AI) based neural network having interconnected nodes, and assemblies of nodes, representing layers of the neural network, including machine learning (ML) or deep learning (DL) models. In a particular embodiment, the ML or neural network model herein may be implemented as a convolution neural network (CNN).

In accordance with a first example embodiment, provided is a method of training a machine learning neural network (MLNN) in monitoring fall characteristics of a subject in motion using mmWave radar sensing techniques. The method is performed in one or more processors of a computing device and comprises receiving, in a first set of input layers of the MLNN, from a millimeter wave (mmWave) radar sensing device, a set of mmWave radar point cloud data representing respective ones of a set of fall attributes associated with a subject, each of the first set of input layers being associated with the respective ones of the set of fall attributes; receiving, at a second set of input layers of the MLNN, a set of personal attributes of the subject, each of the set of personal attributes being associated with a respective one of the second set of input layers, the first and second sets of input layers being interconnected with an output layer of the MLNN via at least one intermediate layer, the at least one intermediate layer configured in accordance with an initial matrix of weights, the first and second sets of input layers, the at least one intermediate and output layers of the MLNN being implemented, using the one or more processors, in a memory of the computing device; training a MLNN classifier in accordance with a supervised training that establishes a correlation between at least one injury condition of the subject as generated at the output layer and the sets of mmWave point cloud data and personal attributes; and adjusting the initial matrix of weights by backpropagation thereby to increase the correlation between the at least one injury condition and the sets of mmWave point cloud data and personal attributes.

In embodiments, the backpropagation comprises recursively adjusting the initial matrix of weights in diminishment of an error matrix calculated at the output layer thereby to increase the correlation between the at least one injury condition, the set of mmWave point cloud data, and the set of personal attributes.

In some aspects, the set of fall attributes includes identification of at least one anatomical member that receives an impact upon falling, a speed at which the at least one anatomical member receives the impact, an orientation of the at least one anatomical member receives the impact, a compliance attribute of a surface at which the impact is received, In variations, the set of fall attributes as monitored via the mmW radar sensor device for the subject comprise progressive timestamps correlated with the mmWave point cloud data representative of bodily dynamic motion characteristics during a fall.

In embodiments, the set of personal attributes can include one or more of a fall subject's age and sex, a weight, a height, a bodily weight distribution profile, and at least one pre-existing medical condition associated with the subject.

In some aspects, the fall injury condition comprises one or more of a skeletal trauma type, a muscular trauma type, and an anatomical organ trauma type.

In embodiments, supervised training of the MLNN classifier comprises correlating the fall attributes as represented by mmWave radar sensing and the personal attributes as received via input layers of the MLNN model with resultant observed fall injury conditions.

In some aspects, the method further comprises deploying the trained MLNN classifier upon establishing the correlation with the fall injury exceeds a 90 percent threshold correlation value.

In some variations, the method further comprises deploying the trained MLNN classifier upon receiving, from a fall of a subsequent subject, a subsequent set of mmWave point cloud data at the first set of input layers and a subsequent set of personal attributes at the second set of input layers in accordance with the trained MLNN.

In yet another embodiment, the method further comprises generating, at the output layer, a fall injury condition attributable to the subsequent subject, such that the trained MLNN model as deployed can be used to diagnose or predict expected attendant fall injuries for a particular subject.

In accordance with a second example embodiment, a non-transitory medium storing instructions executable in a processor of a server computing device is provided. The instructions, when executed in one or more processors, cause operations comprising receiving, in a first set of input layers of the MLNN, from a millimeter wave (mmWave) radar sensing device, a set of mmWave radar point cloud data representing respective ones of a set of fall attributes associated with a subject, each of the first set of input layers being associated with the respective ones of the set of fall attributes; receiving, at a second set of input layers of the MLNN, a set of personal attributes of the subject, each of the set of personal attributes being associated with a respective one of the second set of input layers, the first and second sets of input layers being interconnected with an output layer of the MLNN via at least one intermediate layer, the at least one intermediate layer configured in accordance with an initial matrix of weights, the first and second sets of input layers, the at least one intermediate and output layers of the MLNN being implemented, using the one or more processors, in the memory; training a MLNN classifier in accordance with a supervised training that establishes a correlation between at least one injury condition of the subject as generated at the output layer and the sets of mmWave point cloud data and personal attributes; and adjusting the initial matrix of weights by backpropagation thereby to increase the correlation between the at least one injury condition and the sets of mmWave point cloud data and personal attributes.

In accordance with a third example embodiment, provided is a computing system comprising one or more processors and a memory storing a set of instructions. The instructions when executed in the one or more processors cause operations comprising receiving, in a first set of input layers of the MLNN, from a millimeter wave (mmWave) radar sensing device, a set of mmWave radar point cloud data representing respective ones of a set of fall attributes associated with a subject, each of the first set of input layers being associated with the respective ones of the set of fall attributes; receiving, at a second set of input layers of the MLNN, a set of personal attributes of the subject, each of the set of personal attributes being associated with a respective one of the second set of input layers, the first and second sets of input layers being interconnected with an output layer of the MLNN via at least one intermediate layer, the at least one intermediate layer configured in accordance with an initial matrix of weights, the first and second sets of input layers, the at least one intermediate and output layers of the MLNN being implemented, using the one or more processors, in the memory; training a MLNN classifier in accordance with a supervised training that establishes a correlation between at least one injury condition of the subject as generated at the output layer and the sets of mmWave point cloud data and personal attributes; and adjusting the initial matrix of weights by backpropagation thereby to increase the correlation between the at least one injury condition and the sets of mmWave point cloud data and personal attributes.

One or more embodiments described herein provide that methods, techniques, and actions performed by a computing device are performed programmatically, or as a computer-implemented method. Programmatically, as used herein, means through the use of code or computer-executable instructions. These instructions can be stored in one or more memory resources of the computing device.

Furthermore, one or more embodiments described herein may be implemented through the use of logic instructions that are executable by one or more processors of a computing device, including a server computing device. These instructions may be carried on a computer-readable medium. In particular, machines shown with embodiments herein include processor(s) and various forms of memory for storing data and instructions. Examples of computer-readable mediums and computer storage mediums include portable memory storage units, and flash memory. A server computing device as described herein utilizes processors, memory, and logic instructions stored on computer-readable medium. Embodiments described herein may be implemented in the form of computer processor-executable logic instructions or programs stored on computer memory mediums.

System Description

Figure 1:
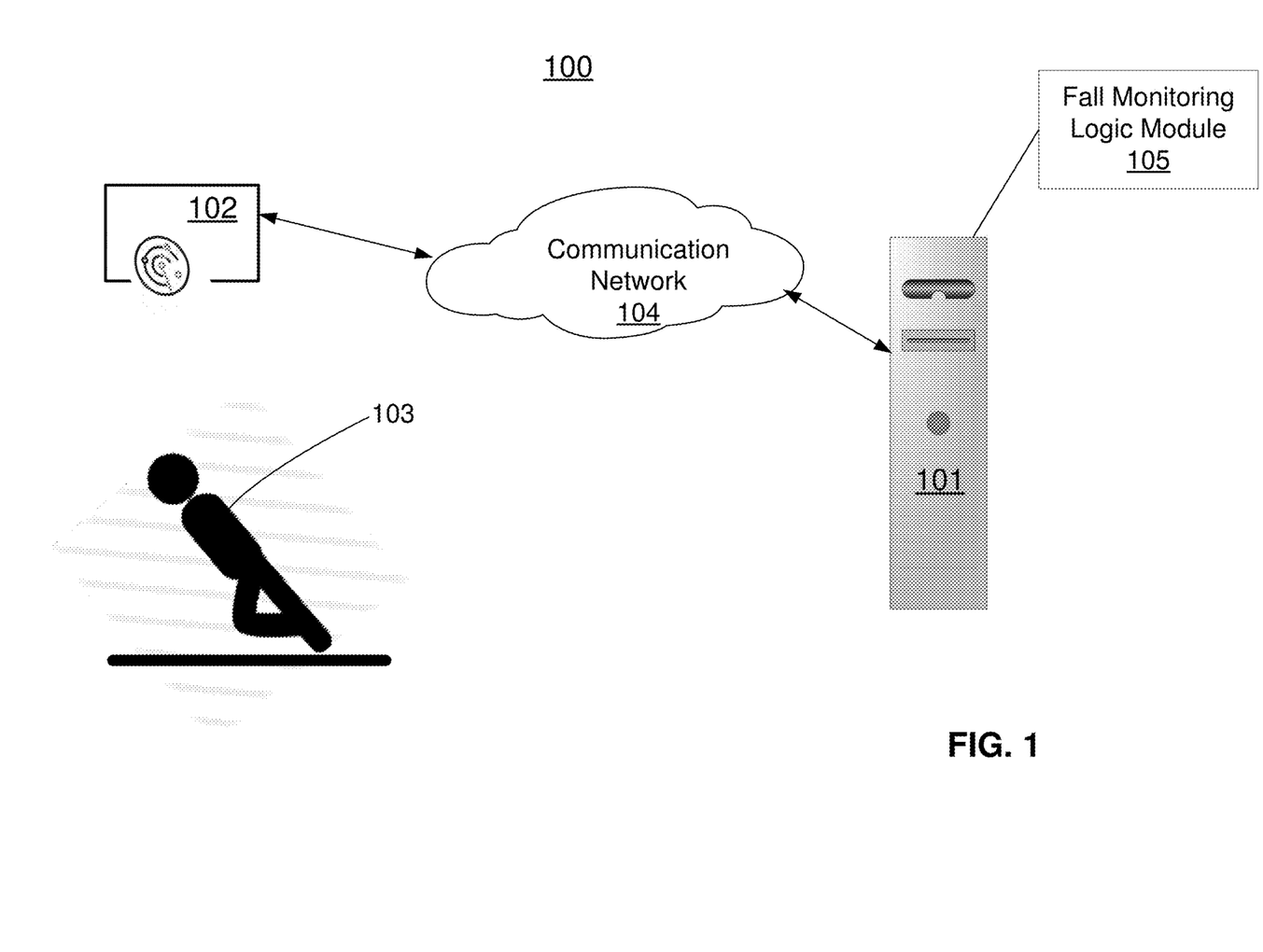
FIG. 1 illustrates, in an example embodiment, a system for training a machine learning neural network (MLNN) in monitoring fall characteristics.

FIG. 1 illustrates, in an example embodiment, system 100 for training a machine learning neural network (MNLL) in monitoring fall characteristics. Server computing system or server device 101, also referred to herein as server 101, includes fall monitoring logic module 105 embodied according to computer processor-executable instructions stored within a non-transitory memory. Server 101 is in communication via communication network 104 with mmWave sensing and communication device 102, sensing and monitoring dynamic fall parameters or attributes of a subject 103, such as a medical patient. In some embodiments, mmWave sensing and communication device 102 can be configured of multiple mmWave sensors working in coordination.

Figure 2:
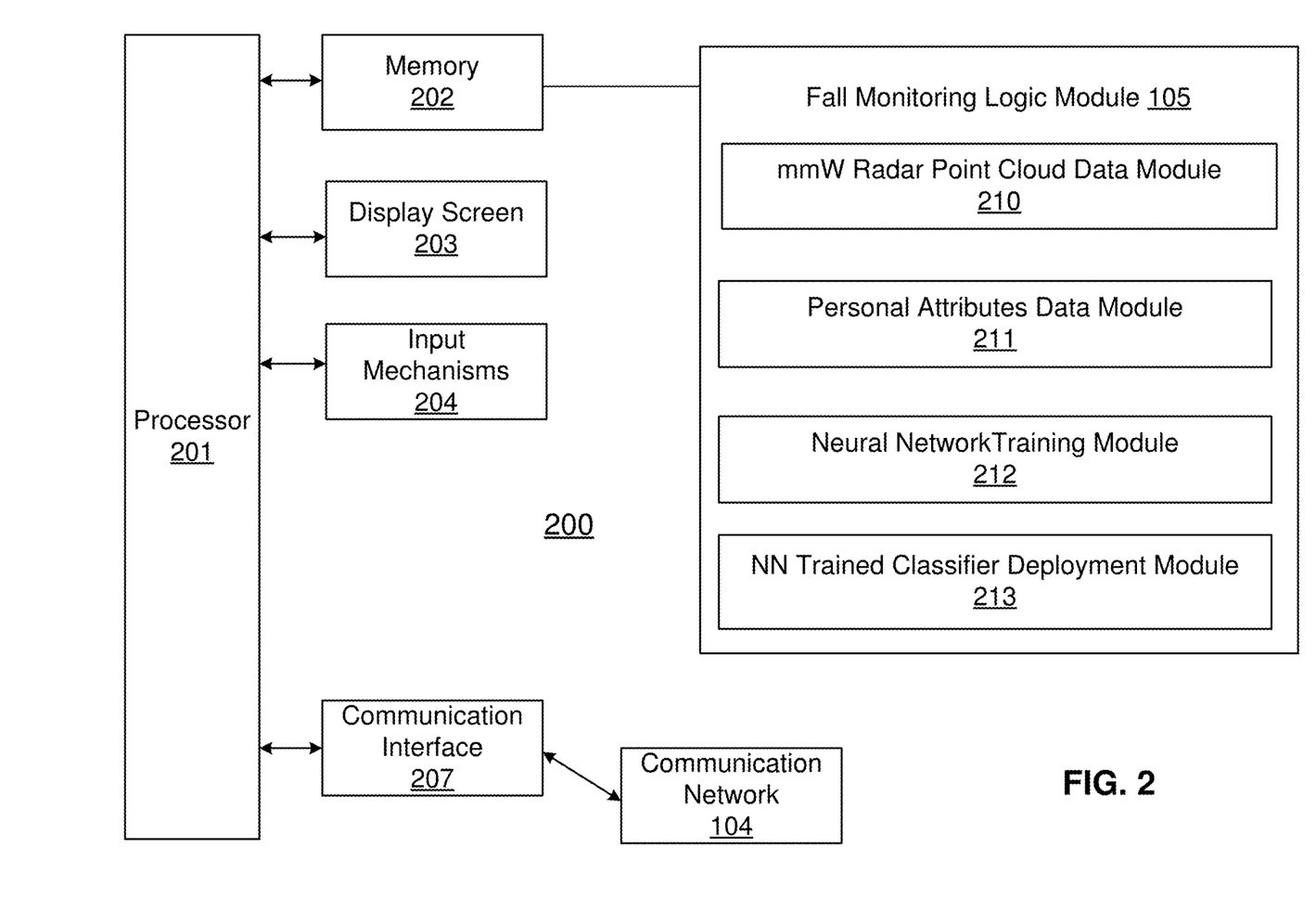
FIG. 2 illustrates, in one example embodiment, an architecture of a system for training a machine learning neural network (MLNN) in monitoring fall characteristics.

FIG. 2 illustrates, in one example embodiment, an architecture of system 200 for training a machine learning neural network (MNLL) in monitoring fall characteristics. Server computing system or device 101, also referred to herein as server 101, may include processor 201, memory 202, display screen 203, input mechanisms 204 such as a keyboard or software-implemented touchscreen input functionality, and communication interface 207 for communicating via communication network 104. Memory 202 may comprise any type of non-transitory system memory, storing instructions that are executable in processor 201, including such as a static random access memory (SRAM), dynamic random access memory (DRAM), synchronous DRAM (SDRAM), read-only memory (ROM), or a combination thereof.

Fall monitoring logic module 105 includes processor-executable instructions stored in memory 202 of server 101, the instructions being executable in processor 201. Fall monitoring logic module 105 can comprise portions corresponding to sub-modules including mmWave radar point cloud data module 210, personal attributes data module 211, neural network training module 212, and neural network trained classifier deployment module 213.

Processor 201 uses executable instructions of mmWave radar point cloud data module 210 to receive, in a first set of input layers of the MLNN, from a millimeter wave (mmWave) radar sensing device, a set of mmWave radar point cloud data representing respective ones of a set of fall attributes associated with a subject, each of the first set of input layers being associated with the respective ones of the set of fall attributes. In embodiments, a respective input layer of the MLNN model can be dedicated to each fall attribute as sensed. Fall attributes of a falling subject as sensed via mmWave radar can include fall speed, the speed of various bodily portions, extremities and limbs, speed of any bodily portions upon impact with the impacted surface, and angular speed of rotation of the subject's body or body portions prior to and upon impact with the surface. The model can also take into account a degree of compliance of the surface upon which the subject falls, such as a hard floor, concrete, a soft surface, a hard edge, a glass surface, among others.

Processor 201 uses executable instructions stored in personal attributes data module 211 to receive, at a second set of input layers of the MLNN, a set of personal attributes of the subject, each of the set of personal attributes being received at a respective one of the second set of input layers. In embodiments, the first and second sets of input layers are interconnected with an output layer of the MLNN via at least one intermediate layer, the at least one intermediate layer being configured in accordance with an initial matrix of weights. The first and second sets of input layers, the at least one intermediate and output layer of the MLNN can be implemented, using the one or more processors, in a memory of the computing device. The MLNN, in embodiments herein, refer to an artificial intelligence (AI) based neural network having interconnected nodes, and assemblies of nodes, representing layers of the neural network, such as the input layers, output layer and intermediate layers interconnecting said input and output layers as described herein.

Processor 201 uses executable instructions stored in neural network training module 212 to train a MLNN classifier in accordance with a supervised training that establishes a correlation between at least one injury condition of the subject as generated at the output layer and the sets of mmWave point cloud data and personal attributes.

In the particular embodiment of a convolution neural network model, the convolution operation typically embodies two parts of inputs: (i) input feature map data, and (ii) a weight (also referred to as output filter, or kernel). Given the input channel data with W (Width)×H (Height)×IC data cube and R×S×IC filter, the output of direct convolution may be formulated as:

$$y_{w,h} = \sum_{r=0}^{R-1}\sum_{s=0}^{S-1}\sum_{c=0}^{C-1} x_{(w+r),(h+s),c} * W_{r,s,c}$$

where:
X=input data/input feature/input feature map
w=width of the input or output data
h=height of the input or output data
R=weight size (width)
S=weight size (height)
C=number of input channel
Y=output data/output feature/output feature map
W=filter/kernel/weight For each input channel, the filter, or weight, are convoluted with data and generates output data. The same location of data of all the input channels are summed together and generate 1 output data channel.

The weight or filter is applied to correlate fall characteristics that include anatomical fall dynamics, or fall attributes as referred to herein, of a particular subject in motion with a likelihood of a specific resultant fall injury condition, based on an input data stream of mmWave radar point cloud data representing sensed fall characteristics of the subject's body in motion as a fall progresses. The particular subject can be associated with particular personal attributes provided via a second input stream of data to the MLNN, such as weight and sex, height, a bodily weight distribution profile, a general state of heath, or even a pre-existing medical condition.

Each output channel of the convolution model is represented by an output filter or weight used to detect one particular feature or pattern of the input feature data stream. Convolution neural networks constituted of interconnected node assemblies can include many output filters or weights for each layer of the convolution model corresponding to respective features or patterns in the data stream of input features.

In embodiments, training the neural network classifier comprises recursively adjusting the initial matrix of weights by backpropogation in diminishment of a number of the false positive vulnerability defects generated at the output layer in accordance with the supervised classification.

In some embodiments, the backpropagation comprises a backward propagation of errors in accordance with an error matrix as computed at the output layer, the errors being distributed backwards throughout the weights of the at least one neural network intermediate layer.

Figure 3:
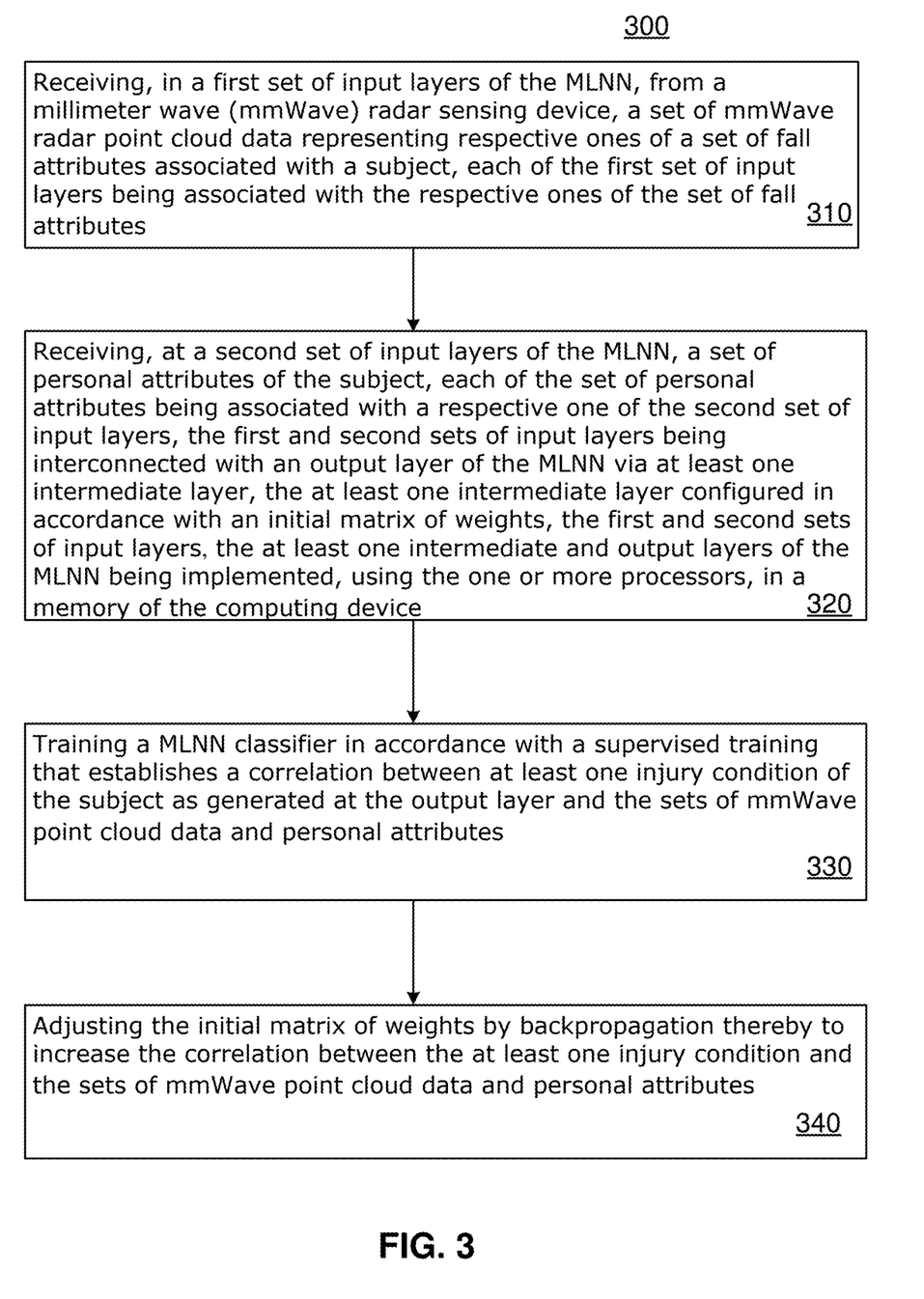
FIG. 3 illustrates a method of operation, in one example embodiment, of a system for training a machine learning neural network (MLNN) in monitoring fall characteristics.

Processor 201 uses executable instructions stored in neural network trained classifier deployment module 213 to adjust the initial matrix of weights by backpropagation thereby to increase the correlation between the at least one injury condition and the sets of mmWave point cloud data and personal attributes Methodology FIG. 3 illustrates method 300 of operation, in one example embodiment, of a system for training a machine learning neural network (MNLL) in monitoring fall characteristics, method 300 being performed by one or more processors 201 of server computing device 101. In describing and performing the embodiments of FIG. 3, the examples of FIG. 1 and FIG. 2 are incorporated for purposes of illustrating suitable components or elements for performing a step or sub-step being described.

Examples of method steps described herein relate to the use of server 101 for implementing the techniques described. According to one embodiment, the techniques are performed by fall monitoring logic module 105 of server 101 in response to the processor 201 executing one or more sequences of software logic instructions that constitute fall monitoring logic module 105.

In embodiments, fall monitoring logic module 105 includes the one or more sequences of instructions within sub-modules including mmWave radar point cloud data module 210, neural network training module 212 and NN trained classifier deployment module 213. Such instructions may be read into memory 202 from machine-readable medium, such as memory storage devices. In executing the sequences of instructions contained in mmWave radar point cloud data module 210, neural network training module 212 and NN trained classifier deployment module 213 of fall monitoring logic module 105 in memory 202, processor 201 performs the process steps described herein. In alternative implementations, at least some hard-wired circuitry may be used in place of, or in combination with, the software logic instructions to implement examples described herein. Thus, the examples described herein are not limited to any particular combination of hardware circuitry and software instructions.

At step 310, processor 201 executes instructions of mmWave radar point cloud data module 210 to receive, in a first set of input layers of the MLNN, from a millimeter wave (mmWave) radar sensing device, a set of mmWave radar point cloud data representing respective ones of a set of fall attributes associated with a subject, each of the first set of input layers being associated with the respective ones of the set of fall attributes.

In some aspects, the set of fall attributes includes identification of at least one anatomical member that receives an impact upon falling, a speed at which the at least one anatomical member receives the impact, an orientation of the at least one anatomical member receives the impact, a compliance attribute of a surface at which the impact is received, In variations, the set of fall attributes as monitored via the mmW radar sensor device for the subject comprise progressive timestamps correlated with the mmWave point cloud data representative of bodily dynamic motion characteristics during a fall.

A mmWave radar sensor is applied herein to produce point clouds, of varying density of data points in embodiments, by making repeated measurements as the body and body members of a medical patient or subject moves, each time acquiring the motion data, correlated via timestamping as progressively sensed, from a different viewpoint or perspective. mm Wave sensor devices transmit an RF signal and record reflection from the target point that is collected in the point cloud, the point cloud data including an object range, angle, velocity, signal strength delivered, and optionally a pre-designated subject ID in one embodiment, over a computing and communication interface. The subject ID may be a patient ID in some embodiments. In embodiments herein, the point cloud data can encapsulate fall dynamics in conjunction with progressive timestamps correlated with the fall data, such that fall dynamic parameters or attributes can be determined, such as but not limited to identification of an anatomical member that receives an impact upon falling, a speed at which the anatomical member receives the impact, an orientation of the anatomical member upon receiving the impact, an angular speed of rotation at which the anatomical member receives the impact, and even a compliance attribute of a surface at which the impact is received. In this manner, the point cloud data as sensed provides an observed time series of bodily portions or members during a fall.

Dynamic parameters associated with a falling subject, also referred to herein as fall attributes, as sensed via mmWave radar and encoded via the point cloud data can include identification of an anatomical member that receives an impact upon falling, a speed at which the anatomical member receives the impact, an orientation of the anatomical member upon receiving the impact, an angular speed of rotation at which the anatomical member receives the impact, and even a compliance attribute of a surface at which the impact is received At step 320, processor 201 of server computing device 101 executes instructions of personal attributes data module 211, in some embodiments generally concurrently with step 310, to receive, at a second set of input layers of the MLNN, a set of personal attributes of the subject, each of the set of personal attributes being associated with a respective one of the second set of input layers. In embodiments, the first and second sets of input layers are interconnected with an output layer of the MLNN via at least one intermediate layer, the at least one intermediate layer configured in accordance with an initial matrix of weights. The first and second sets of input layers, the at least one intermediate and output layers of the MLNN can be implemented, using the one or more processors, in a memory of the computing device. The MLNN, in embodiments herein, refer to an artificial intelligence (AI) based neural network having interconnected nodes, and assemblies of nodes, representing layers of the neural network, such as, but not limited to, the input layers, output layer and intermediate layers interconnecting said input and output layers as described herein.

In embodiments, the set of personal attributes can include one or more of a fall subject's age and sex, a weight, a height, a bodily weight distribution profile, and at least one pre-existing medical condition associated with the subject.

At step 330, processor 201 executes instructions included in neural network training module 212 to train a MLNN classifier in accordance with a supervised training that establishes a correlation between at least one injury condition of the subject as generated at the output layer and the sets of mmWave point cloud data and personal attributes. In some aspects, the fall injury condition comprises one or more of a skeletal trauma type, a muscular trauma type, and an anatomical organ trauma type.

In embodiments, supervised training of the MLNN classifier comprises correlating the fall attributes as represented by mmWave radar sensing and the personal attributes as received via input layers of the MLNN model with resultant actual fall injury conditions as observed.

At step 340, processor 201 executes instructions included in neural network trained classifier deployment module 213 to adjust the initial matrix of weights by backpropagation thereby to increase the correlation between the at least one injury condition and the sets of mmWave point cloud data and personal attributes.

In embodiments, the backpropagation comprises recursively adjusting the initial matrix of weights in diminishment of an error matrix calculated at the output layer thereby to increase the correlation between the fall injury condition(s), the set of mmWave point cloud data, and the set of personal attributes.

In some embodiments, the mmWave radar sensing device comprises a 60 GHz mmWave radar sensing device.

The neural networks of embodiments herein refer to an artificial intelligence (AI) based neural network, including machine learning (ML) or deep learning (DL) models, constituted of interconnected nodes, and assemblies of nodes. In a particular embodiment, the ML or neural network model herein may be implemented as a convolution neural network (CNN).

Figure 4:
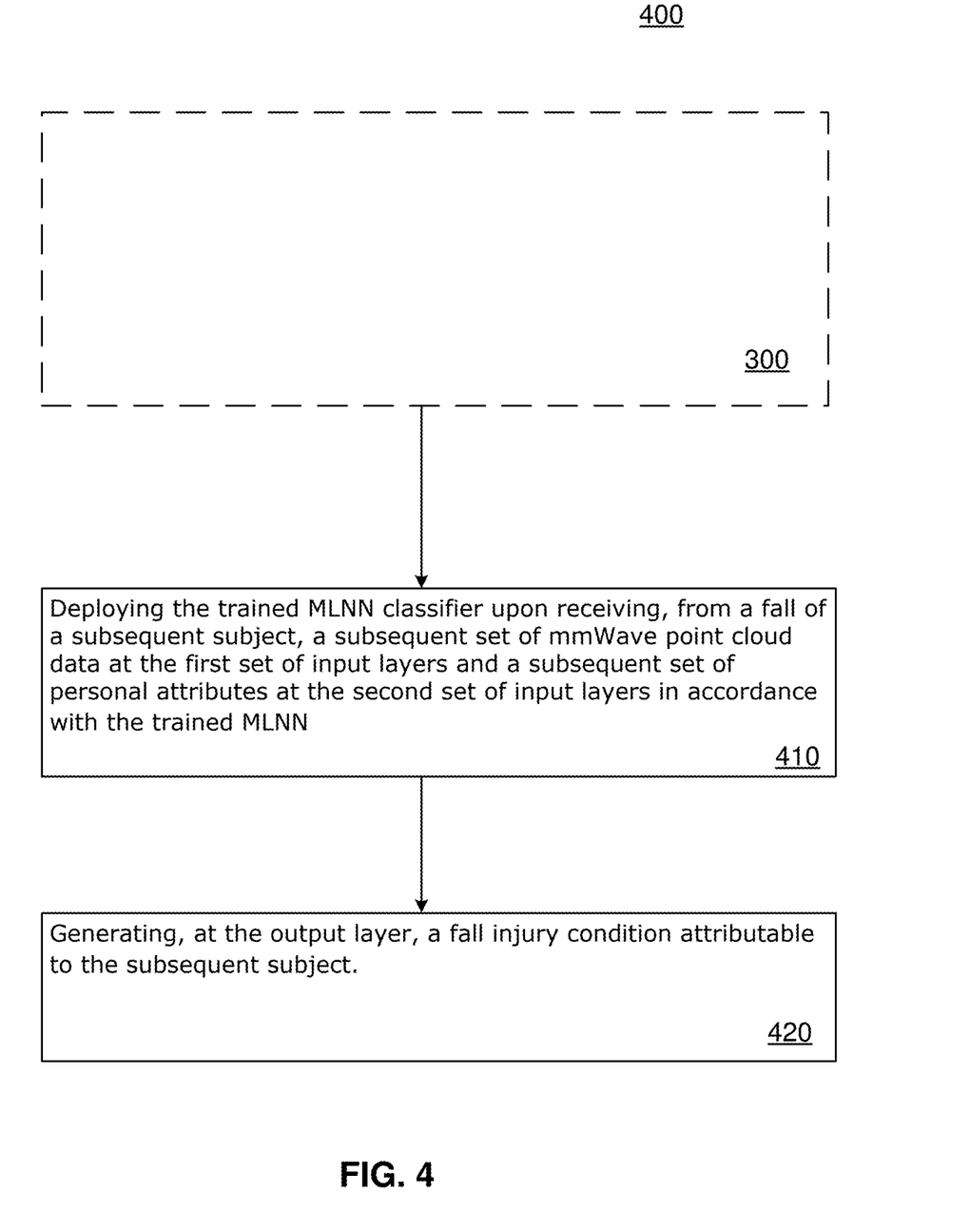
FIG. 4 illustrates a method of operation, in one example embodiment, for deploying a trained machine learning neural network (MLNN) in predicting injury conditions based on fall characteristics.

FIG. 4 illustrates method 400 of operation, in one example embodiment, for deploying a trained machine learning neural network (MNLL) in predicting injury conditions based on fall characteristics, using the trained classifier in conjunction with the disclosures of FIGS. 1-3. In some aspects, such deploying proceeds once the MLNN trained classifier, based on the supervised training as described herein with regard to FIG. 3, for example, produces a sufficiently high correlation in predicting fall injuries with high enough accuracy of prediction. In one embodiment, the deploying proceeds when the trained classifier attains at least a correlation threshold limit of 90 percent likelihood of predicting a sufficient set or range of fall injuries.

At step 410, deploying the trained MLNN classifier upon receiving, from a fall of a subsequent subject, a subsequent set of mmWave point cloud data at the first set of input layers and a subsequent set of personal attributes at the second set of input layers in accordance with the trained MLNN.

At step 420, generating, at the output layer, a fall injury condition attributable to the subsequent subject, such that the trained MLNN model as deployed can be used to diagnose or predict expected attendant fall injuries.

In additional embodiments, the system 100 can determine and generate a statistical confidence factor associated with a particular diagnosis or prediction by the MLNN of the fall injury condition attributable to the subject of the fall, based at least in part on historical data. Based on input parameters for fall attributes and personal attributes that are within certain standard deviations in a normal statistical distribution based on previous falls diagnosed.

It is contemplated that embodiments described herein extend to individual elements and concepts described herein, as well as for embodiments to include combinations of elements, features and techniques recited herein. Although embodiments are described in detail herein with reference to the accompanying drawings, it is to be understood that the invention is not limited to only such example embodiments. Accordingly, many modifications and variations will be apparent to practitioners skilled in the art. As such, it is intended that the scope of the invention be defined by the following claims and their equivalents. Furthermore, it is contemplated that a particular feature described either individually or as part of an embodiment can be combined with other individually described features, or parts of other embodiments, even if the other features and embodiments make no mention of the particular feature. Thus, absence of particular describing combinations does not preclude the inventors from claiming rights to such combinations.

What is claimed is:

1. A method of deploying a trained machine learning neural network (MLNN) in generating a fall injury condition of a subject, the method performed in one or more processors of a computing device and comprising:

receiving, in a first set of input layers of the trained MLNN, a set of millimeter wave (mmWave) radar point cloud data representing a set of fall attributes based on monitoring the subject using a mmWave radar sensing device, each of the first set of input layers being associated with respective ones of the set of fall attributes;

receiving, at a second set of input layers of the trained MLNN, a set of personal attributes of the subject, each of the set of personal attributes being associated with a respective one of the second set of input layers, the first and second sets of input layers being interconnected with an output layer of the trained MLNN via at least one intermediate layer, the at least one intermediate layer, the at least one intermediate and output layers of the trained MLNN being instantiated in a memory of the computing device, the trained MLNN produced based at least in part upon establishing a correlation between at least one injury condition of a set of prior subjects as generated at the output layer and respective sets of mmWave point cloud data and personal attributes associated with the set of prior subjects; and generating, at the output layer, the fall injury condition attributable to the subject.

2. The method of claim 1 wherein the at least one intermediate layer is configured in accordance with an initial matrix of weights.

3. The method of claim 2 wherein the trained MLNN is produced in accordance with adjusting the initial matrix of weights by backpropagation thereby to increase the correlation between the at least one injury condition and the sets of mmWave point cloud data and personal attributes associated with the set of prior subjects.

4. The method of claim 3 wherein the backpropagation comprises recursively adjusting the initial matrix of weights in diminishment of an error matrix calculated at the output layer thereby to increase the correlation between the at least one injury condition, the set of mmWave point cloud data, and the set of personal attributes associated with the set of prior subjects.

5. The method of claim 1 wherein the set of fall attributes includes identification of at least one anatomical member that receives an impact upon falling, a speed at which the at least one anatomical member receives the impact, an orientation of the at least one anatomical member receives the impact, an angular speed of rotation at which the at least one anatomical member receives the impact, a compliance attribute of a surface at which the impact is received.

6. The method of claim 1 wherein the set of fall attributes as monitored via the mmWave radar sensing device for the subject comprise progressive timestamps associated with the sets of mmWave point cloud data.

7. The method of claim 1 wherein the set of personal attributes include at least one of an age, a weight, a height, a bodily weight distribution profile, and at least one pre-existing medical condition associated with the subject.

8. The method of claim 1 wherein the injury condition comprises at least one of a skeletal trauma type, a muscular trauma type, and an anatomical organ trauma type.

9. The method of claim 1 wherein the trained MLNN is produced in accordance with a supervised training that comprises correlating the fall attributes as represented by mmWave radar sensing and the personal attributes associated with the set of prior subjects with resultant observed fall injury conditions.

10. The method of claim 1 wherein the trained MLNN is produced in accordance with a convolution neural network configuration.

11. A computing system comprising:
one or more processors;
a memory storing a set of instructions, the instructions when executed in the one or more processors causing operations comprising:
receiving, in a first set of input layers of a trained MLNN, a set of millimeter wave (mmWave) radar point cloud data representing a set of fall attributes based on monitoring a subject using a mmWave radar sensing device, each of the first set of input layers being associated with respective ones of the set of fall attributes;

receiving, at a second set of input layers of the trained MLNN, a set of personal attributes of the subject, each of the set of personal attributes being associated with a respective one of the second set of input layers, the first and second sets of input layers being interconnected with an output layer of the trained MLNN via at least one intermediate layer, the at least one intermediate layer, the at least one intermediate and output layers of the trained MLNN being instantiated in the memory of the computing system, the trained MLNN produced based at least in part upon establishing a correlation between at least one injury condition of a set of prior subjects as generated at the output layer and respective sets of mmWave point cloud data and personal attributes associated with the set of prior subjects; and generating, at the output layer, a fall injury condition attributable to the subject.

12. The computing system of claim 11 wherein the at least one intermediate layer is configured in accordance with an initial matrix of weights.

13. The computing system of claim 12 wherein the trained MLNN is produced in accordance with adjusting the initial matrix of weights by backpropagation thereby to increase the correlation between the at least one injury condition and the sets of mmWave point cloud data and personal attributes associated with the set of prior subjects.

14. The computing system of claim 13 wherein the backpropagation comprises recursively adjusting the initial matrix of weights in diminishment of an error matrix calculated at the output layer thereby to increase the correlation between the at least one injury condition, the set of mmWave point cloud data, and the set of personal attributes associated with the set of prior subjects.

15. The computing system of claim 11 wherein the set of fall attributes includes identification of at least one anatomical member that receives an impact upon falling, a speed at which the at least one anatomical member receives the impact, an orientation of the at least one anatomical member receives the impact, an angular speed of rotation at which the at least one anatomical member receives the impact, a compliance attribute of a surface at which the impact is received.

16. The computing system of claim 11 wherein the set of fall attributes as monitored via the mmWave radar sensing device for the subject comprise progressive timestamps associated with the sets of mmWave point cloud data.

17. The computing system of claim 11 wherein the set of personal attributes include at least one of an age, a weight, a height, a bodily weight distribution profile, and at least one pre-existing medical condition associated with the subject.

18. The computing system of claim 11 wherein the injury condition comprises at least one of a skeletal trauma type, a muscular trauma type, and an anatomical organ trauma type.

19. The computing system of claim 11 wherein the trained MLNN is produced in accordance with a supervised training that comprises correlating the fall attributes as represented by mmWave radar sensing and the personal attributes associated with the set of prior subjects with resultant observed fall injury conditions.

20. The computing system of claim 11 wherein the trained MLNN is produced in accordance with a convolution neural network configuration.

* * * * *